United States Patent
Thesen

(10) Patent No.: US 7,501,821 B2
(45) Date of Patent: Mar. 10, 2009

(54) **METHOD FOR DETERMINATION OF THE TRANSVERSE RELAXATION TIME T2* IN MR DATA**

(75) Inventor: Stefan Thesen, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 153 days.

(21) Appl. No.: 11/613,333

(22) Filed: Dec. 20, 2006

(65) Prior Publication Data

US 2007/0152666 A1 Jul. 5, 2007

(30) Foreign Application Priority Data

Dec. 20, 2005 (DE) .................. 10 2005 060 986

(51) Int. Cl.
*G01V 3/00* (2006.01)

(52) U.S. Cl. .................. 324/309; 324/310; 324/307

(58) Field of Classification Search ......... 324/300–322; 600/410–423, 9.3
See application file for complete search history.

(56) References Cited

U.S. PATENT DOCUMENTS

| 5,270,654 | A | * | 12/1993 | Feinberg et al. | .............. | 324/309 |
| 5,565,777 | A | | 10/1996 | Kanayama et al. | .......... | 324/309 |
| RE35,656 | E | * | 11/1997 | Feinberg et al. | .............. | 324/309 |
| 5,860,921 | A | | 1/1999 | Ma et al. | ..................... | 600/410 |
| 6,169,398 | B1 | * | 1/2001 | Watanabe et al. | ........... | 324/309 |
| 7,332,909 | B2 | * | 2/2008 | Schaffter et al. | ............. | 324/309 |
| 2005/0033156 | A1 | | 2/2005 | Kruger et al. | ................ | 600/410 |
| 2006/0034765 | A1 | * | 2/2006 | Schmainda et al. | .......... | 424/9.3 |
| 2006/0273790 | A1 | * | 12/2006 | Eggers et al. | ................ | 324/309 |
| 2007/0080685 | A1 | * | 4/2007 | Bydder et al. | ................ | 324/309 |
| 2007/0152666 | A1 | * | 7/2007 | Thesen | ....................... | 324/307 |
| 2007/0247153 | A1 | * | 10/2007 | Yu et al. | ..................... | 324/307 |

FOREIGN PATENT DOCUMENTS

| EP | 1 136 836 | | 9/2001 |
| WO | WO 2004095048 | A1 * | 11/2004 |
| WO | WO 2006/018780 | | 2/2006 |

OTHER PUBLICATIONS

"Removal of Local Field Gradient Artifacts in $T_2*$—Weighted Images at High Fields by Gradient-Echo Slice Excitation Profile Imaging," Yang et al, Magnetic Resonance In Medicine, vol. 39 (1998) pp. 402-409.

"Rapid Simultaneous Mapping of $T_2$ and $T_2*$ by Multiple Acquisition of Spin and Gradient Echoes Using Interleaved Echo Planar Imaging (Masage-IEPI)," Thomas et al, NeuroImage, vol. 15 (2002) pp. 992-1002.

* cited by examiner

*Primary Examiner*—Diego Gutierrez
*Assistant Examiner*—Tiffany A Fetzner
(74) *Attorney, Agent, or Firm*—Schiff Hardin LLP

(57) ABSTRACT

In a method for determination of the transverse relaxation time T2* in MR data, the T2* relaxation is detected in a measurement volume and the transverse relaxation time is determined from the time curve of the magnetization in the measurement volume. In order to be able to more reliably determine the transverse relaxation time T2*, a local magnetic field in the measurement volume is determined and the transverse relaxation time is corrected dependent on the local magnetic field such that a corrected transverse relaxation time is obtained. The local magnetic field is determined by determination of the phase curve of the magnetization from multiple predetermined echo times, the echo times having different intervals ($\Delta TE$) from one another, and determination of the local magnetic field from the phase curve of the magnetization. The interval between the echo times at least at one point in the measurement volume is adapted such that the local magnetic field can be determined without phase compression.

9 Claims, No Drawings

METHOD FOR DETERMINATION OF THE TRANSVERSE RELAXATION TIME T2* IN MR DATA

BACKGROUND OF THE INVENTION

1. Field of the Invention

The present invention concerns a method for determination of the transverse relaxation time T2* in MR data.

2. Description of the Prior Art

The determination of the transverse relaxation time T2* in magnetic resonance measurements (MR) is suitable, for example, for diagnosis of thalassemia. Thalassemia is a genetically contingent abnormality in the hemoglobin production. Untreated patients possibly suffer from anemia that is accompanied by an increased iron concentration in the myocardium. Treatment of the illness with an iron chelation therapy is possible. An iron concentration that is too high is thereby decreased by suitable medications. If a concentration is too high untreated, the risk of a cardiac arrest exists. If the concentration is too low, the risk exists of an over-treatment that can lead to, for example, kidney failure and other side effects.

As a series of studies show, particularly information about the iron concentration in the myocardium is relevant for a successful therapy. A change in the iron concentration results in a shortening of the T2* time has a magnetic resonance measurement (data acquisition). Exact quantitative information about the iron concentration does not presently appear to be possible; but a classification of the state of the patient based on the T2* time in the clinic appears to be possible. In the literature a determination of the T2* time in the myocardium by means of magnetic resonance measurements is therefore advocated as a diagnostic and therapy modality.

The problem has been conventionally solved by the following approach. The signal of the myocardium is acquired with a T2*-sensitive sequence (free induction decay, FID) at various echo times. A value for T2* can be determined using an exponential function. A single shot EPI (echoplanar imaging) sequence is described in the literature as advantageous. Data with different echo times are acquired with constant repetition time. The data are acquired at the end of diastole in order to minimize flow and movement artifacts. The acquisition in a single breath-hold phase is advantageous. The magnitude images are then manually corrected for movement. A sector in the myocardium is selected, typically in the septum. An average value is calculated from the magnitude data for each echo time and a fit with an exponential function is implemented. The decay constant is used as a value for T2*.

Disagreements as to the validity of the determined T2* values exists in the literature and the scientific community.

The precise determination of T2* is viewed as extremely problematic since many other effects in addition to the local iron concentration have an influence on this value (for example magnetic field homogeneity). Local dependencies of the B0 field that are not dependent on the local iron concentration in the myocardium occur in particular due to susceptibility effects, for example of the lungs and in general of the surrounding anatomy. Moreover, this effect cannot be completely cancelled by a fine tuning of the field homogeneity (shimming). Due to these effects, the determined T2* time can vary significantly thereby interfering with the clinically-relevant value (T2* of the myocardium).

A method for determination of the transverse relaxation time T2* in MR data is known from U.S. Pat. No. 5,565,777 that includes the steps: of detection of the T2* relaxation in a measurement volume; determination of the relaxation time from the time curve of the magnetization in the measurement volume; determination of the local magnetic field in the measurement volume and correction of the relaxation time dependent on the local magnetic field such that a corrected transverse relaxation time results. The local magnetic field is determined by the steps of determination of the phase curve of the magnetization for multiple predetermined echo times (TE), the echo times having different intervals ($\Delta TE$) from one another, and determination of the local magnetic field from the phase curve of the magnetization.

U.S. Pat. No. 5,860,921 describes a method for measurement of the reversible contribution to the transverse relaxation time in MR imaging methods. The transverse relaxation time T2* is corrected dependent on the local magnetic field according to the formula:

$$(1/T2^* \text{ observed}) \approx (1/T2^* \text{ corrected}) + \gamma \pi \Delta B0.$$

A method for MR imaging with gradient echoes with which T2-weighted MR images can be generated very quickly is known from EP 1 136 836 A2.

SUMMARY OF THE INVENTION

An object of the present invention is to provide a method with which the T2* time can be determined reliably and independent of apparatus parameters and surrounding anatomy.

The invention is based on the approach of correcting the T2* values dependent on the actual local magnetic field present at the measurement location. The local magnetic field is thereby either determined by measurement thereof or it is extracted from the measurement data for T2* determination.

The inventive method for determination of the transverse relaxation time T2* in MR data including the steps of detection of the temporally variable transversal magnetization in a measurement volume; determination of the transverse relaxation time from the time curve of the magnetization in the measurement volume; determination of a local magnetic field in the measurement volume; and correction of the transverse relaxation time dependent on the local magnetic field, such that a corrected transverse relaxation time results. The local magnetic field is determined by the steps of determination of the phase curve of the magnetization using multiple predetermined echo times (TE), the echo times having different intervals ($\Delta TE$) from one another, and determination of the local magnetic field from the phase curve of the magnetization, with a region adjacent to the measurement volume being used as a reference.

The inventive method has, among other things, the advantage that it enables the correction of effects due to the local magnetic field and is thereby more robust, i.e. is independent of anatomy and MR system. Moreover, it is also suited for determination of the local magnetic field.

DESCRIPTION OF THE PREFERRED EMBODIMENTS

The T2* time is typically determined with a gradient echo sequence. The decay constant T2* can be concluded via observation of the decay time (FID) given different echo times.

In practice the magnetic field varies from location to location such that different precession frequencies of the nuclear magnetic resonance result. A shortened induction decrease is therefore observed as a consequence of destructive interference. In order to differentiate from the global effects, the measured T2* must be corrected, This ensues according to the relation:

$$(1/T2^* \text{ observed}) \approx (1 T2^* \text{ corrected}) + \gamma \pi \Delta B0 \qquad (1),$$

wherein $\Delta B0$ is the deviation from the assumed magnetic field at the measurement location. A complete modeling of the T2* relaxation generally also takes B0 effects into account.

In accordance with the invention, the local magnetic field is determined from the phase information of the measurement data acquired for T2* determination. In this measurement a gradient echo is acquired at various times TE. In addition to he information about the amplitude (magnitude) of the magnetization, in this manner information about the phase of the magnetization is moreover obtained.

The time curve of the phase at various echo times can be used for quantitative determination of the local magnetic field (of the B0 field) at the measurement location. A sufficiently dense staggering of the echo times (at least in one region) is possibly necessary. The deviation of the actual resonance frequency from the set resonance frequency can be determined in points (per pixel) from the echo time difference ΔTE of the employed scan values according to the relation $$\Delta v = \Delta\phi/(2\pi \cdot \Delta TE) \qquad (2),$$

wherein Δv is the frequency deviation, Δϕ is the change of the phase angle and ΔTE is the time interval between the echo times. The actual resonance frequency then can be determined from the frequency deviation and the set resonance frequency. The absolute value B0 of the local magnetic field thus can also be determined by the gyromagnetic ratio γ.

In an alternative embodiment of the invention, for T2* determination a separate measurement is implemented for determination of the local magnetic field from the measurement data. For this in particular the measurement for electrical fine tuning of the field homogeneity is used.

In both embodiments above, spatially-resolved information about the deviation of the local magnetic field is acquired. With this known deviation the measured T2* for each voxel is corrected according to the relation (1).

For an examination such as a thalassemia examination, data are acquired at different echo times in a slice (short axial section) of the heart with constant repetition rate. A B0 field map is calculated voxel-by-voxel per region from the phase evolution. This is advantageously suitably processed further by adaptation of a model function and by smoothing, etc. At the same time a T2* map is generated per voxel or per region from the magnitude data. This map is corrected with knowledge of the local B0 field distribution. A diagnosis then can be made using the corrected T2* values.

In the clinical examination, a comparison of the measurement with a reference is made. For this purpose, a region in the ventricle directly adjacent to the region under consideration in the myocardium is used. This serves as a reference. Instead of the T2* value, a derived quantity from the T2* values of the myocardium and the reference region is used (for example a quotient).

In an alternative embodiment a blood sample is taken and its iron content or T2* is examined ex vivo such that precise data about the reference are available.

For calibration of the inventive method, in particular the echo time differences are adapted at least at one point, such that the B0 field can be determined without phase compression having to be taken into account.

In order to mask effects from the different resonance frequencies of fat and water, the echo time differences ΔTE at at least one point are advantageously (a) selected so small or (b) selected such that both fat protons and water protons have rotated further in this time by a whole-number multiple of 2π (in-phase condition).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining the transverse relaxation time T2* in magnetic resonance data, comprising the steps of:
    detecting a T2* relaxation in a measurement volume of a subject, said measurement volume exhibiting a magnetization while said T2* relaxation is being detected;
    determining a local magnetic field in said measurement volume by determining a phase curve of said magnetization in said measurement volume for a plurality of predetermined echo times having respectively different time intervals from one another and determining the local magnetic field in the measurement volume from said phase curve, and adapting the interval between respective echo times for at least one point in said measurement volume, to allow determination of said local magnetic field without phase compressions, by selecting said interval between said respective echo times to produce an in-phase condition; and
    correcting said T2* relaxation time dependent on said local magnetic field, to obtain a correct transverse relaxation time T2*.

2. A method as claimed in claim 1 comprising determining said local magnetic field with a measurement for electrical fine tuning of a field homogeneity in said measurement volume.

3. A method as claimed in claim 1 comprising determining a frequency deviation of an actual resonance frequency used to detect the T2* relaxation time in the measurement volume, from a set resonance frequency, according to:

$$\Delta v = \Delta\phi/(2\pi \cdot \Delta TE),$$

wherein Δv is said frequency deviation, Δϕ is a change of the phase angle and ΔTE is said time interval between echo times, and determining said local magnetic field from said frequency deviation Δv.

4. A method as claimed in claim 1 comprising correcting the transverse relaxation time T2* detected in the measurement volume dependent on the local magnetic field according to:

$$(1/T2^* \text{ observed}) \approx (1/T2^* \text{ corrected}) + \gamma\pi\Delta B0,$$

wherein γ is the gyromagnetic ratio and ΔB0 represents a deviation in homogeneity of a basic magnetic field that exists during detection of said T2* relaxation time in said measurement volume.

5. A method as claimed in claim 1 comprising detecting said magnetization in said measurement volume with a constant repetition rate.

6. A method as claimed in claim 1 comprising, in a computer, adapting a model function to measurement values for determining said local magnetic field.

7. A method as claimed in claim 1 comprising using a region adjacent to said measurement volume as a reference against which the corrected T2* relaxation time is compared.

8. A method as claimed in claim 1 comprising obtaining a T2* relaxation time from a blood sample of the subject and using the T2* relaxation time obtained from said blood sample as a reference against which said corrected T2* relaxation time is compared.

9. A method as claimed in claim 1 comprising detecting said T2* relaxation time in a plurality of volume elements of predetermined size in said measurement volume, with a measurement value being obtained from each measurement volume, and smoothing said measurement values over a totality of said volume elements.

* * * * *